(12) United States Patent
Harr

(10) Patent No.: US 10,426,709 B2
(45) Date of Patent: Oct. 1, 2019

(54) FEEDING SET AND ENTERAL FEEDING PUMP

(71) Applicant: KPR U.S., LLC, Mansfield, MA (US)

(72) Inventor: James Harr, Wentzville, MO (US)

(73) Assignee: KPR U.S., LLC, Mansfield, MA (US)

( * ) Notice: Subject to any disclaimer, the term of this patent is extended or adjusted under 35 U.S.C. 154(b) by 0 days.

(21) Appl. No.: 15/805,895

(22) Filed: Nov. 7, 2017

(65) Prior Publication Data
US 2018/0060516 A1 Mar. 1, 2018

Related U.S. Application Data

(62) Division of application No. 14/494,993, filed on Sep. 24, 2014, now Pat. No. 9,852,263.
(Continued)

(51) Int. Cl.
A61F 15/00 (2006.01)
A61J 15/00 (2006.01)
(Continued)

(52) U.S. Cl.
CPC ...... A61J 15/0076 (2015.05); A61M 5/14232 (2013.01); G06F 19/3475 (2013.01);
(Continued)

(58) Field of Classification Search
CPC .............. G06F 19/3406; G06F 19/3475; A61J 15/0076; A61J 2205/60; A61J 2200/76;
(Continued)

(56) References Cited

U.S. PATENT DOCUMENTS 4,108,575 A 8/1978 Schal
4,256,437 A 3/1981 Brown
(Continued)

FOREIGN PATENT DOCUMENTS

CN 101306211 A 11/2008
CN 101628137 A 1/2010
WO 2015053616 A1 4/2015

OTHER PUBLICATIONS

Abbott Nutrition Corporate Website, Abbott-Companion Enteral Nutrition Pump, Oct. 24, 2008, http://obottnutrition.com/ph/1 0/08/ 2009-11-16-46 35691 %20Companion%200perating%20Manual% 202008.pdf, 13 pages.
(Continued)

Primary Examiner — Amber R Stiles

(57) ABSTRACT

A feeding set for use with a peristaltic enteral feeding pump to deliver nutritional liquid fluid to a patient includes a container having nutritional liquid. A conduit assembly includes tubing placeable in fluid communication with the container and adapted for mounting on the enteral feeding pump. The tubing provides a fluid pathway for delivering the nutritional liquid from the container to a patient when the tubing is mounted on the enteral feeding pump. An identification member is mounted on the conduit assembly and has at least one characteristic of a nutritional liquid associated with the feeding set represented by the identification member. The identification member is positioned on the conduit assembly so as to permit automatic identification by the enteral feeding pump of the at least one characteristic of the nutritional liquid upon mounting the conduit assembly on the enteral feeding pump.

19 Claims, 6 Drawing Sheets

Related U.S. Application Data

(60) Provisional application No. 61/881,590, filed on Sep. 24, 2013.

(51) Int. Cl.
*A61M 5/142* (2006.01)
*G06F 19/00* (2018.01)
*G16H 40/63* (2018.01)

(52) U.S. Cl.
CPC .......... *G16H 40/63* (2018.01); *A61J 2200/76* (2013.01); *A61J 2205/60* (2013.01); *A61M 2205/14* (2013.01); *A61M 2205/60* (2013.01); *A61M 2205/6054* (2013.01); *Y10T 29/49117* (2015.01)

(58) Field of Classification Search
CPC .......... A61M 5/14232; A61M 2205/14; A61M 2205/60; A61M 2205/6054; Y10T 29/49117
See application file for complete search history.

(56) References Cited

U.S. PATENT DOCUMENTS

| | | | |
|---|---|---|---|
| 4,460,355 A | 7/1984 | Layman |
| 4,613,325 A | 9/1986 | Abrams |
| 4,634,426 A | 1/1987 | Kamen |
| 4,755,172 A | 7/1988 | Baldwin |
| 4,976,590 A | 12/1990 | Baldwin |
| 4,976,687 A | 12/1990 | Martin |
| 5,024,347 A | 6/1991 | Baldwin et al. |
| 5,181,910 A | 1/1993 | Scanlon |
| 5,201,711 A | 4/1993 | Pasqualucci et al. |
| 5,213,483 A | 5/1993 | Flaherty et al. |
| 5,312,334 A | 5/1994 | Hara et al. |
| 5,389,078 A | 2/1995 | Zalesky et al. |
| 5,395,320 A | 3/1995 | Padda et al. |
| 5,429,602 A | 7/1995 | Hauser |
| 5,460,490 A | 10/1995 | Carr et al. |
| 5,499,968 A | 3/1996 | Milijasevic et al. |
| 5,514,102 A | 5/1996 | Winterer et al. |
| 5,531,680 A | 7/1996 | Dumas et al. |
| 5,562,615 A | 10/1996 | Nassif |
| 5,586,872 A | 12/1996 | Skobelev et al. |
| 5,630,711 A | 5/1997 | Luedtke et al. |
| 5,658,250 A | 8/1997 | Blomquist et al. |
| 5,720,721 A | 2/1998 | Dumas et al. |
| 5,755,563 A | 5/1998 | Clegg et al. |
| 5,772,635 A | 6/1998 | Dastur et al. |
| 5,807,321 A | 9/1998 | Stoker et al. |
| 5,842,841 A | 12/1998 | Danby et al. |
| 5,871,465 A | 2/1999 | Vasko |
| 5,885,245 A | 3/1999 | Lynch et al. |
| 5,993,422 A | 11/1999 | Schafer |
| 6,019,582 A | 2/2000 | Green |
| 6,142,752 A | 11/2000 | Akamatsu et al. |
| 6,228,057 B1 | 5/2001 | Vasko |
| 6,283,719 B1 | 9/2001 | Frantz et al. |
| 6,436,072 B1 | 8/2002 | Kullas et al. |
| 6,468,242 B1 | 10/2002 | Wilson et al. |
| 6,523,414 B1 | 2/2003 | Malmstrom et al. |
| 6,659,976 B2 | 12/2003 | Beck et al. |
| 6,749,410 B1 | 6/2004 | Burch |
| 6,752,779 B2 | 6/2004 | Paukovits et al. |
| 6,758,655 B2 | 7/2004 | Sacher |
| 6,768,425 B2 | 7/2004 | Flaherty et al. |
| 6,790,198 B1 | 9/2004 | White et al. |
| 6,852,094 B2 | 2/2005 | Beck et al. |
| 6,997,905 B2 | 2/2006 | Gillespie et al. |
| 7,029,455 B2 | 4/2006 | Flaherty |
| 7,070,575 B2 | 7/2006 | Beck et al. |
| 7,092,796 B2 | 8/2006 | Vanderveen |
| 7,092,797 B2 | 8/2006 | Gaines et al. |
| 7,118,347 B2 | 10/2006 | Solgaard et al. |
| 7,121,143 B2 | 10/2006 | Malmstrom et al. |
| 7,356,382 B2 | 4/2008 | Vanderveen |
| 7,396,512 B2 | 7/2008 | Ditrolio et al. |
| 7,447,566 B2 | 11/2008 | Knauper et al. |
| 7,462,170 B2 | 12/2008 | Fournie et al. |
| 7,645,258 B2 | 1/2010 | White et al. |
| 7,753,880 B2 | 7/2010 | Malackowski |
| 7,753,881 B2 | 7/2010 | Fournie et al. |
| 7,753,883 B2 | 7/2010 | Fournie et al. |
| 7,771,386 B2 | 8/2010 | Eggers et al. |
| 7,794,423 B2 | 9/2010 | Gaines et al. |
| 7,927,304 B2 | 4/2011 | Hudson et al. |
| 8,021,322 B1* | 9/2011 | Francis ............... G06F 19/3468 604/66 |
| 8,025,634 B1 | 9/2011 | Moubayed et al. |
| 8,574,190 B2 | 11/2013 | Francis |
| 2002/0169636 A1 | 11/2002 | Eggers et al. |
| 2003/0078534 A1 | 4/2003 | Hochman et al. |
| 2006/0073048 A1* | 4/2006 | Malackowski .... A61B 17/1626 417/474 |
| 2006/0278221 A1 | 12/2006 | Schermeier et al. |
| 2008/0119822 A1 | 5/2008 | Knauper |
| 2008/0139997 A1 | 6/2008 | Sacchetti |
| 2009/0030366 A1 | 1/2009 | Hochman |
| 2009/0171289 A1 | 7/2009 | Davis et al. |
| 2009/0221986 A1 | 9/2009 | Wang et al. |
| 2010/0280486 A1 | 11/2010 | Khair et al. |
| 2011/0196291 A1 | 8/2011 | Vischer et al. |
| 2011/0257576 A1 | 10/2011 | Simpson et al. |
| 2012/0078196 A1* | 3/2012 | Fournie .................. A61J 15/00 604/246 |
| 2012/0245554 A1 | 9/2012 | Kawamura |
| 2013/0025357 A1 | 1/2013 | Noack et al. |
| 2014/0031784 A1 | 1/2014 | Flynn et al. |

OTHER PUBLICATIONS

Covidien Corporate Website, Covidien-Kangaroo ePump, Enteral Feeding Pump Frequently Asked Questions, 2009, ttp:/Iwww.kangarooepump.com/pagebuilder.aspx?webPageiD=131038&&topiciD=131038, 3 pages.

Dietscher et al., "Accuracy of Enteral Pumps: In Vitro Performance," Journal of Parenteral and Enteral Nutrition, vol. 8, No. 4, 1994, pp. 359-361.

Examination Report dated Nov. 29, 2017 for European Application No. EP14780738 filed Sep. 24, 2014, 5 pages.

Examiner's Report dated Mar. 3, 2017 in related Canadian Application No. 2925086, 3 pages.

Fresenius-Kabi Corporate Website, Fresenius-Kabi—Enteral Feeding Pumps, Apr. 2010, http://www.fresenius-kabi.com/2202.htm, 6 pages.

International Search Report and Written Opinion for Application No. PCT/US2014/057137, dated Jan. 29, 2015, 12 pages.

Moog Inc. Corporate Website, Moog Inc.—Enteral Feeding Pumps, 2009, http://www.moog.com/products/medicalump-systems/enteral-feeding-pumps/enteralite-infinity/, 12 pages.

Ross Nutrition Corporate Website, Ross Nutrition—Flexiflo Quantum Enteral Pump, 2004, http://www.pristolhomeinfusion.com/images/docs/Quantum-English-manual.pdf- , 20 pages.

Serrano et al., "The Relationship Between the Viscosity of Enteral Nutrition Products and Delays or Interruptions in the infusion Rate Selected," Nutr Hosp., vol. 9, No. 4, Jul.-Aug, 1994, pp. 257-261—abstract only.

Tepaske et al., "Clinically Relevant Differences in Accuracy of Enteral Nutrition Feeding Pump Systems," Journal of Parenteral and Enteral Nutrition, vol. 30, No. 4, 2006, pp. 339-343.

Examination Search Report for Australian Application No. 20140326970, dated Feb. 18, 2019, 4 pages.

Office Action dated Apr. 4, 2018 for Chinese Application No. CN201480052200.X filed Sep. 24, 2014, 20 pages.

* cited by examiner

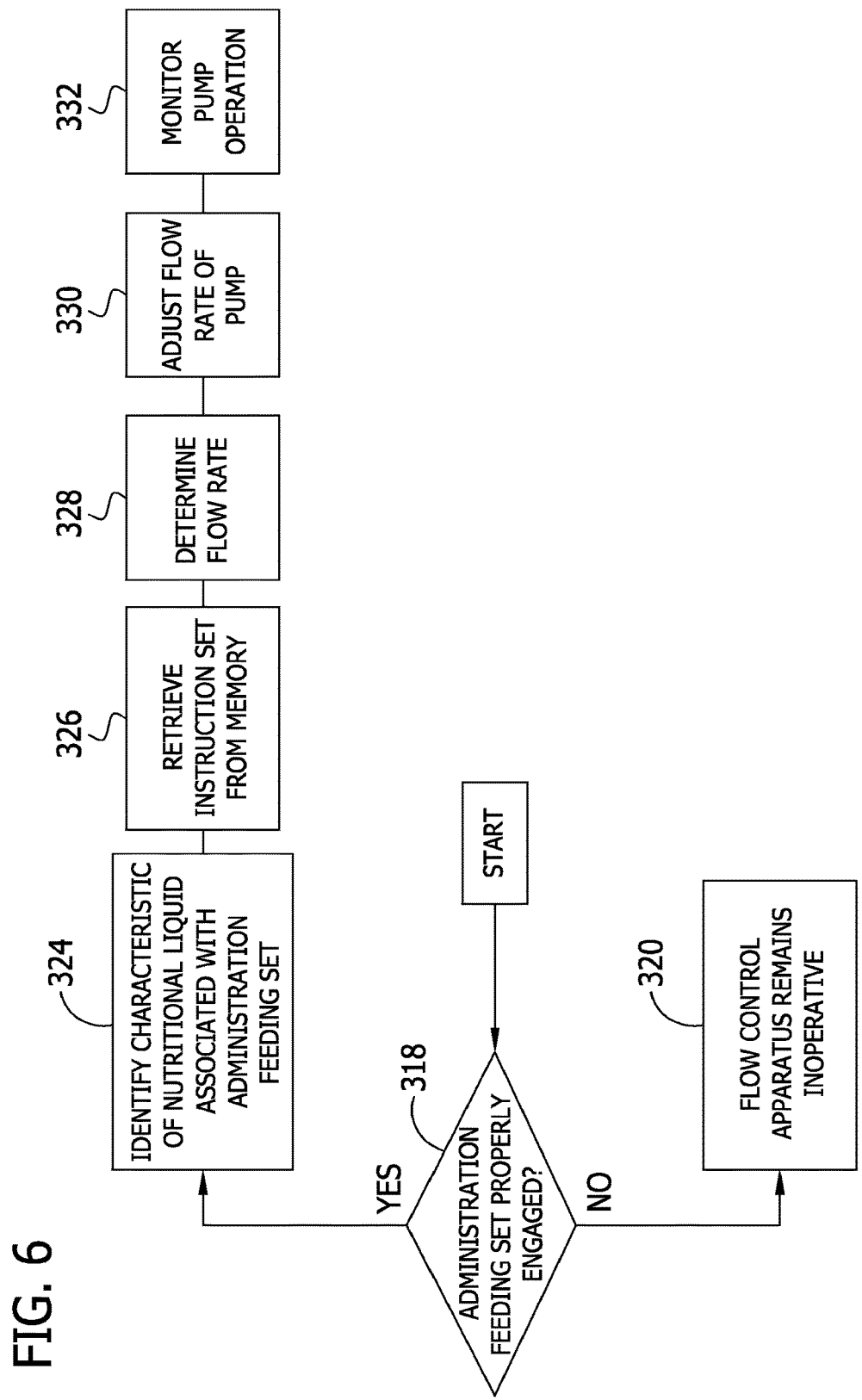

FEEDING SET AND ENTERAL FEEDING PUMP

CROSS-REFERENCE TO RELATED APPLICATIONS

The present application claims priority to U.S. patent application Ser. No. 14/494,993, filed Sep. 24, 2014, which claims the benefit of U.S. Patent Application Ser. No. 61/881,590, entitled Feeding Set and Enteral Feeding Pump, filed Sep. 24, 2013, the complete disclosures of each are incorporated herein by reference for all purposes.

FIELD OF THE INVENTION

This invention relates generally to pumps used to deliver fluids to patients by way of a pump set, and more particularly to use of an identification member with an enteral feeding pump to provide a pump operating profile based on the information in the identification member.

BACKGROUND

Administering fluids to a patient via a patient's nose, mouth, or abdomen is known. Fluids can be delivered to the patient by gravity flow or at a controlled rate of delivery by utilizing a flow control apparatus, such as a peristaltic pump through a feeding set. The feeding apparatus for administering fluids to the patient typically has a housing that includes at least one motor operatively coupled to a mechanism that is engaged with a feeding set by progressively compressing a tubing of the feeding set to drive the fluid through the tubing at the controlled rate. In typical rotary peristaltic pumps, the motor is connected to a shaft that rotatably drives a pump rotor. The rotating pump rotor engages the tubing of the feeding set, pinching off a portion of the tubing and pushing the feeding fluid forward from the pinch point, toward the patient. In this manner, a peristaltic action that is created by the rotation of the rotor drives fluid through the tubing. Such enteral feeding pumps deliver feeding fluids of differing formulation, each of which may have differing characteristics, such as viscosity, nutritional value, caloric content, and other characteristics, which may result in variations in flow behavior.

SUMMARY

Aspects of the present invention generally relate to an enteral feeding system used to deliver enteral fluids to a patient and, particularly, to a feeding set for use in the feeding system having a representation regarding nutritional liquid associated with the feeding set.

In a first aspect, a feeding set for use with an enteral feeding pump to deliver nutritional liquid fluid to a patient generally comprises a container having nutritional liquid. A conduit assembly includes tubing placeable in fluid communication with the container and adapted for mounting on the enteral feeding pump. The tubing provides a fluid pathway for delivering the nutritional liquid from the container to a patient when the tubing is mounted on the enteral feeding pump. An identification member is mounted on the conduit assembly and has at least one characteristic of a nutritional liquid associated with the feeding set represented by the identification member. The identification member is positioned on the conduit assembly to permit automatic identification by the enteral feeding pump of the at least one characteristic of the nutritional liquid upon mounting the conduit assembly on the enteral feeding pump.

In said first aspect, the conduit assembly may include a cassette connected to the tubing.

In said first aspect, the identification member can be mounted on the cassette.

In said first aspect, the identification member can comprise one or more magnets arranged to represent the nutritional liquid in the container.

In said first aspect, the at least one characteristic can comprise the nutritional liquid type.

In said first aspect, the at least one characteristic can comprise a viscosity of the nutritional liquid.

In said first aspect, the at least one characteristic can comprise a caloric content of the nutritional liquid.

In said first aspect, a family of nutritional liquids associated with the feeding set can be represented by the identification member.

In said first aspect in combination with the enteral feeding pump, the enteral feeding pump can include a reader for reading the identification member to identify, which can be automatic, the at least one characteristic of the nutritional liquid associated with the feeding set upon mounting the conduit assembly on the enteral feeding pump.

In said first aspect, the enteral feeding pump can determine, which can be automatic, a flow rate for delivering fluid through the tubing based on the at least one characteristic of the nutritional liquid identified by the enteral feeding pump upon mounting the conduit assembly on the enteral feeding pump.

In said first aspect, the enteral feeding pump can automatically initiate a compliance operation whereby the apparatus monitors a volume of fluid and a number of calories delivered to the patient through the tubing upon mounting the conduit assembly on the enteral feeding pump.

In a second aspect, an enteral feeding pump for use with a nutritional liquid feeding set to deliver nutritional liquid through the feeding set generally comprises a housing capable of receiving at least a portion of the feeding set. A pumping device can be mounted in the housing and configured to act on the feeding set to produce fluid flow in the feeding set when the feeding set is received by the housing. A processor can be operatively connected to the pumping device. A reader can be operatively connected to the processor and can be configured to read the feeding set to facilitate identification of at least one characteristic of the nutritional liquid associated with the feeding set upon engagement of the feeding set with the housing. The processor can be programmed to automatically identify the at least one characteristic upon engagement of the feeding set with the housing.

In said second aspect, the processor can be programmed to select and display a library subset from a library of nutritional liquids stored in memory of the pump. The library subset can be associated with the feeding set engaged with the housing.

In said second aspect, the processor can be programmed to automatically determine a flow rate for delivering fluid through the feeding set based on the identified at least one characteristic of the nutritional liquid associated with the feeding set upon engagement of the feeding set with the housing.

In said second aspect, the processor can be programmed to initiate, automatically, a compliance operation whereby the pump monitors a volume of fluid and a number of calories delivered to the patient through the feeding set upon engagement of the feeding set with the housing.

In a further aspect, a method of providing an enteral feeding pump for use with a nutritional liquid feeding set configured to deliver nutritional liquid from a container through the feeding set comprises mounting a pumping device onto a housing of the pump, the pumping device configured to act on the feeding set to produce fluid flow in the feeding set during operation thereof; disposing a reader on the housing, the reader configured to read the feeding set to identify at least one characteristic of the nutritional liquid associated with the feeding set; and operatively connecting a processor to the reader, wherein the processor is configured to identify the at least one characteristic upon operational engagement of the feeding set with the housing.

In said further aspect, the method can further comprise providing the feeding set, wherein the feeding set comprises an identification member and tubing in fluid communication with the container, wherein the identification member is associated with the nutritional liquid in the container.

In said further aspect, the at least one characteristic can comprise at least one of a viscosity of the nutritional liquid and a caloric content of the nutritional liquid.

In said further aspect, a family of nutritional liquids associated with the feeding set is represented by the identification member.

In said further aspect, the method can further comprise operably connecting a memory to the processor, the memory configurable to include the at least one characteristic of the nutritional liquid to be associated with the feeding set.

In said further aspect, the method can further comprise providing instructions on non-transitory memory that are executable by the processor, the instructions comprising identifying the at least one characteristic of the nutritional liquid associated with the feeding set based on a representation from an identification member on the feeding set; and operating the pump at a flow rate to achieve a target feeding rate based on the at least one characteristic.

In a still further aspect, a non-transitory computer-readable medium is disclosed. The computer-readable medium includes computer-executable instructions for a method of operating a feeding pump with a feeding set having tubing fluidly connected to a container for containing a nutritional liquid to be delivered to a patient when the feeding set is operably mounted on the feeding pump, the feeding set further comprising an identification member readable by a reader on the feeding pump, wherein the identification member provides a representation of nutritional liquid. The method comprises identifying at least one characteristic of the nutritional liquid associated with the feeding set based on a representation from the identification member on the feeding set; and operating the pump at a flow rate to achieve a target feeding rate based on the at least one characteristic. In such still further aspect, the method can further comprise associating the representation from the identification member to one or more nutritional liquids in a library stored in a memory in the pump and identify the at least one characteristic of the nutritional liquid.

Other features will be in part apparent and in part pointed out hereinafter.

BRIEF DESCRIPTION OF THE DRAWINGS

Aspects of the present invention generally relate to an enteral feeding system used to deliver enteral fluids to a patient and, particularly, to a feeding set for use in the feeding system that represents a nutritional liquid associated with the feeding set.

FIG. 6 is a flow chart of a software subsystem illustrating a process used to detect and identify a formula associated with a feeding set adapted to be loaded to a feeding pump, which may be implemented in accordance with one or more aspects disclosed herein.

Corresponding reference characters indicate corresponding parts throughout the drawings.

DETAILED DESCRIPTION

Figure 1:
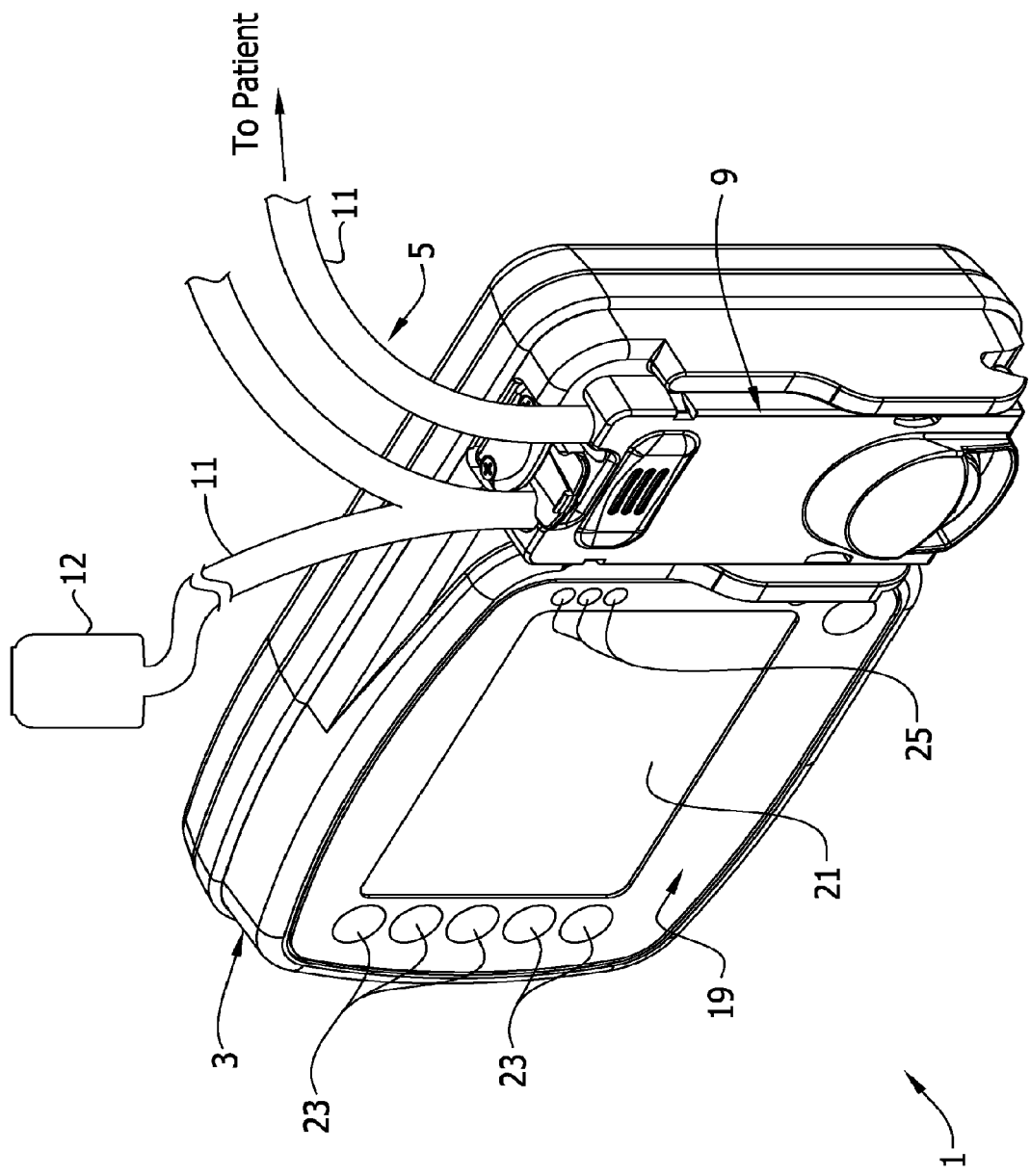
FIG. 1 is a schematic illustration showing a perspective view of an enteral feeding pump and a fragmentary portion of a feeding set received on the pump, in accordance with one or more aspects disclosed herein.
Figure 2:
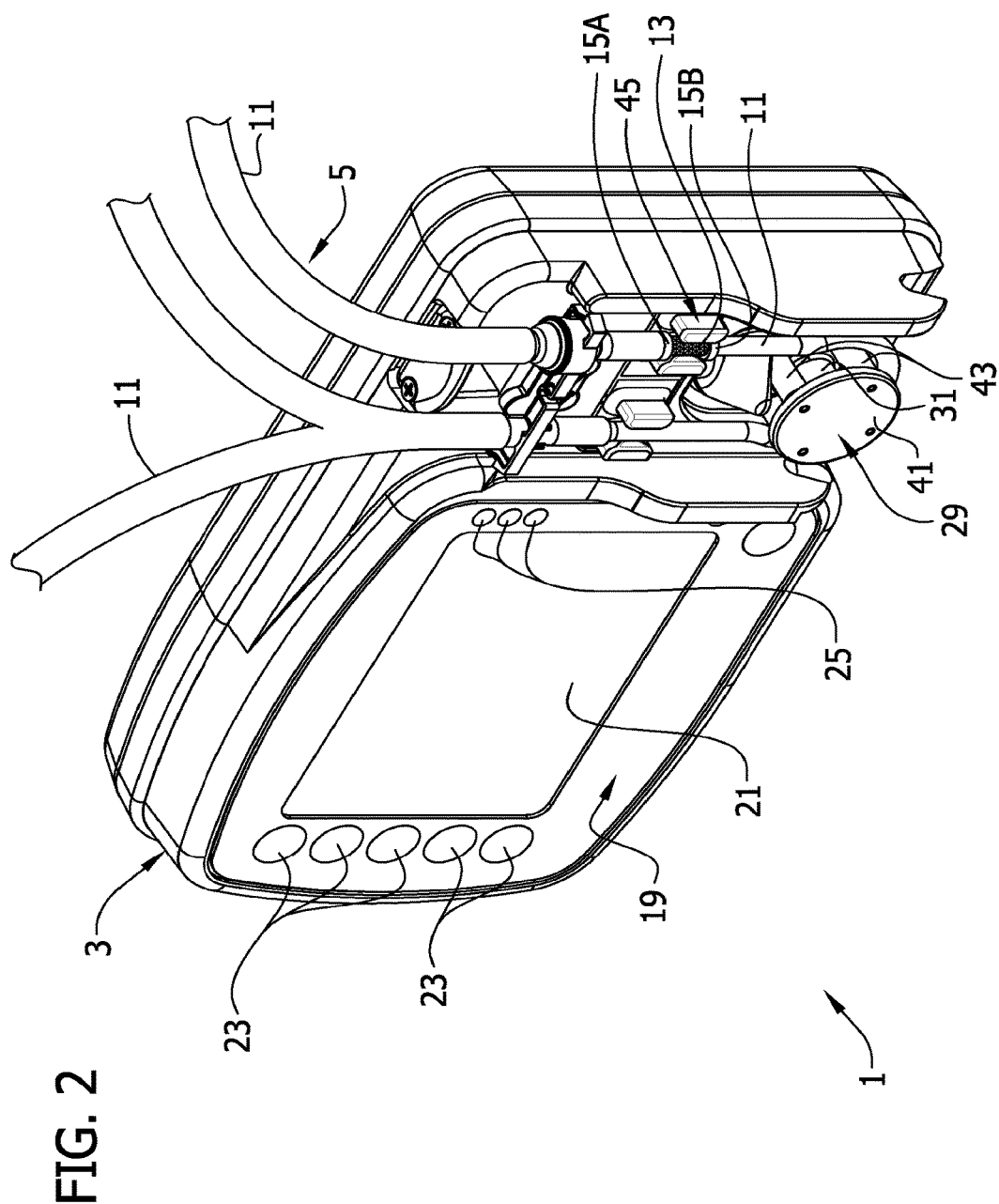
FIG. 2 is schematic illustration showing the pump and feeding set of FIG. 1, with a cassette housing of the feeding set removed.
Figure 3:
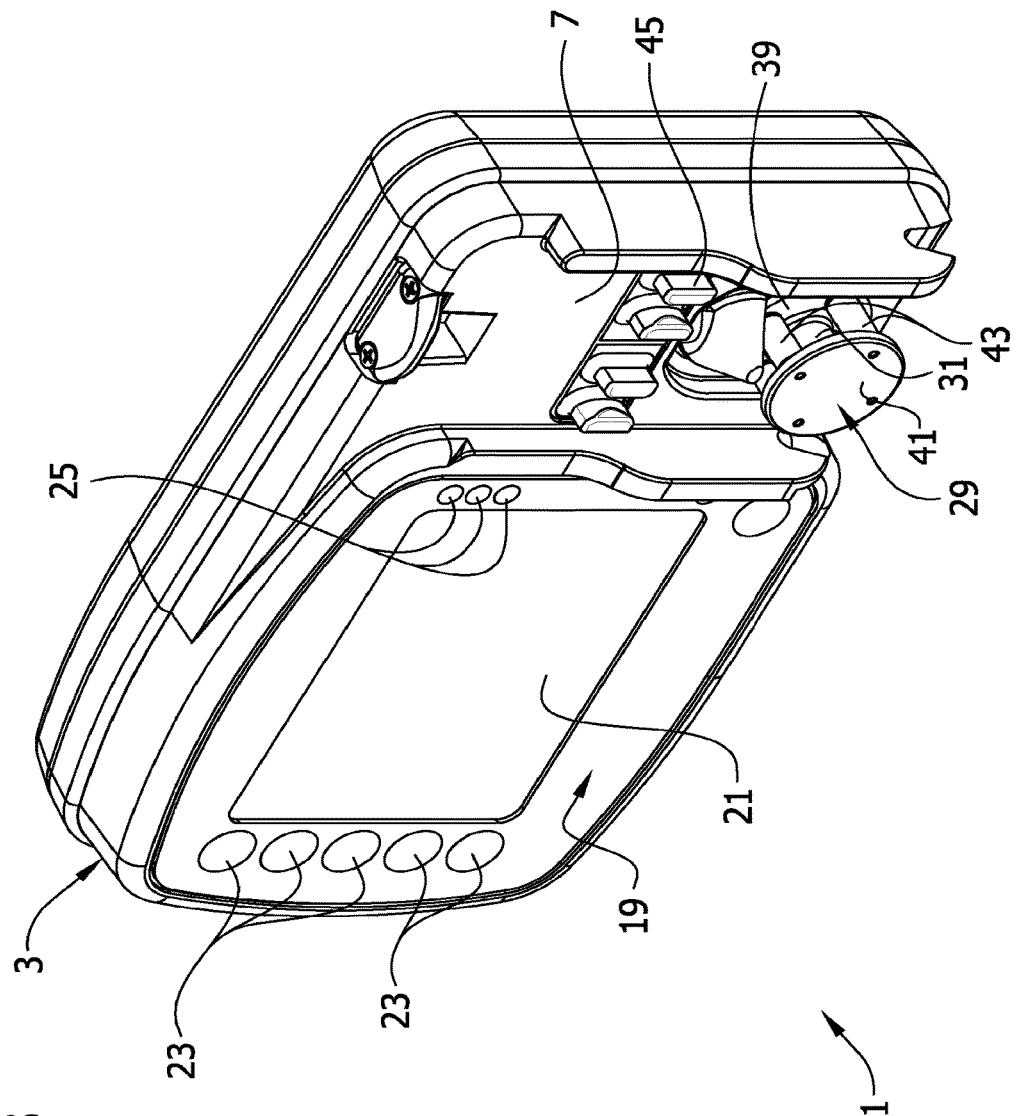
FIG. 3 is schematic illustration showing the pump of FIG. 1, with the feeding set removed.

Referring now to the exemplary embodiment schematically illustrated in FIGS. 1-3, an enteral feeding pump is generally indicated at 1. The pump 1 may comprise a housing 3 that is constructed to allow a feeding set 5 to be mounted to the housing. Optionally, the housing 3 may comprise a recess 7 (FIG. 3) for receiving a cassette 9 of the feeding set 5 to load the feeding set on the pump. The feeding set 5 can comprise tubing indicated generally at 11 that provides a fluidic pathway between a bag 12 of nutritional liquid (broadly, "a container") and a patient (FIG. 1). The bag 12 is shown schematically in FIG. 1. The cassette 9 may facilitate mounting the tubing 11 for engaging the tubing with the pump 1 when received in the recess 7. The cassette 9 and feeding set 5 may be broadly considered a conduit assembly.

The feeding set 5 may comprise a mounting member 13 (FIG. 2) in direct communication with the tubing 11 and one or more identification members 15 on the mounting member. At least one identification member 15 may permit identification of at least one characteristic of a nutritional liquid associated with the feeding set upon engagement of the mounting member 13 to the pump 1. The mounting member 13 may also assist in the loading of the feeding set 5 on the pump 1. However, the mounting member 13 may be omitted and the identification member(s) 15 may be used to load the feeding set 5 to the pump 1. The pump may further include a reader 17 (FIGS. 4 and 5) that detects engagement of at least one of the mounting member 13 and the identification member(s) 15 with the pump.

Depending on the desired feeding regime, feeding sets of different constructions can be used with the pump 1. An effective flow rate for the pump 1 can depend on a resistance of the tubing of the feeding set and the fluid being delivered through the feeding set. The pump 1 can be configured to recognize automatically the type of feeding set installed and a nutritional liquid associated with the feeding set, and alter or tailor operation of the pump to accommodate the characteristics of the feeding set and nutritional liquid. In particular, a flow rate for delivering fluid associated with the loaded feeding set 5 can be automatically customized by retrieving identification information or data represented by the identification member 15 indicating at least one of the type of feeding set, the associated nutritional liquid, and/or characteristics of the nutritional liquid pertaining to delivering the liquid through the feeding set. Such technical feature can advantageously effect delivery of the nutritional liquid to the patient by reducing the likelihood against an inappropriate or erroneous delivery protocol. For example, a feeding set having an identification member can provide a representation of the nutritional liquid in the container connected thereto to the pump which in turn can automatically deliver the nutritional liquid according to a predetermined protocol or schedule, which reduces the likelihood of erroneously delivering the nutritional liquid at a different delivery protocol or schedule.

As used herein, the term "load" means that the tubing 11 is engaged with the pump 1 so that the feeding set 5 is ready for operation with the pump to deliver fluid to a patient. It will be appreciated that the term "housing," as used herein, may include many forms of supporting structures including, without limitation, multi-part structures and structures that do not enclose or house the working components of the pump 1.

The pump 1 may include a user interface 19 with a display screen indicated at 21 on the front of the housing 3 that is capable of displaying information about the status and operation of the pump. The pump 1 can further comprise buttons 23 and light emitting diodes 25 on the housing 3 for use with the display screen 21 to facilitate exchanging information, such as providing and obtaining information, between the pump 1 and a user. Various user interfaces for displaying information to the user and receiving user input may be implemented. Any of the various configurations of the user interface can involve utilizing one or more graphical display subcomponents. As an example, the display screen 21 may be a graphical user interface having a touch screen by which the user can provide the input information. In other embodiments, the user interface can be a tethered component that can be used to provide input information, provide operating information pertaining to the flow control apparatus, or both.

Figure 4:
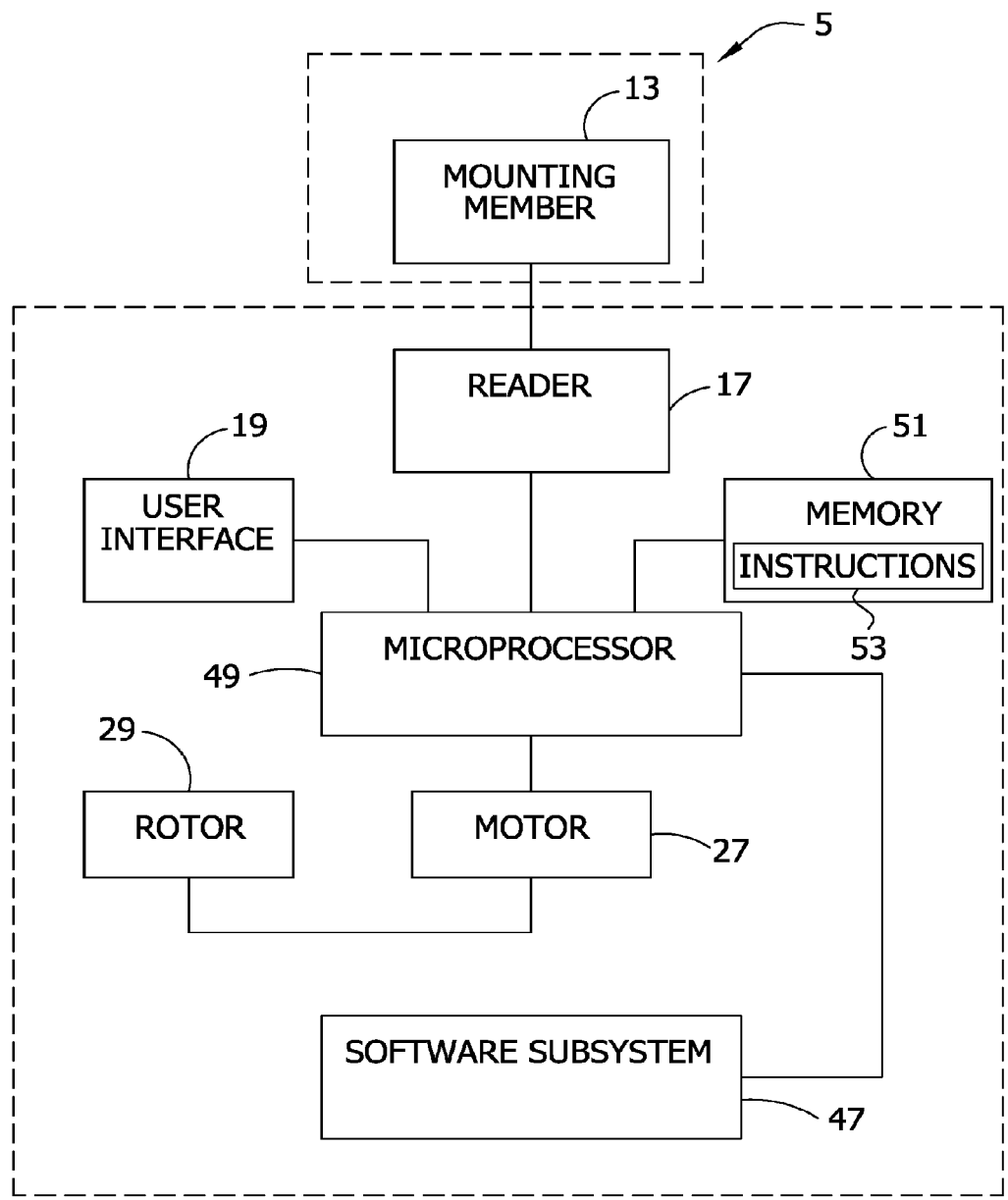
FIG. 4 is a block diagram schematically illustrating the feeding set loaded on the pump.

Referring to FIGS. 2-4, the pump 1 may include a pump motor 27 (FIG. 4) located in the housing 3. A pump rotor 29 may be mounted on a rotatable shaft 31 and rotated by the motor 27. In one embodiment, the pump rotor 29 includes an inner disk 39, an outer disk 41, and preferably a plurality of rollers 43 mounted between the inner and outer disks rotatable about their longitudinal axes relative to the disks. In the exemplarily illustrated embodiment, the pump motor 27, rotatable shaft 31 and pump rotor 29 may broadly be considered a pumping device. The rollers 43 may engage the feeding set 5 for moving fluid through the feeding set.

Figure 5:
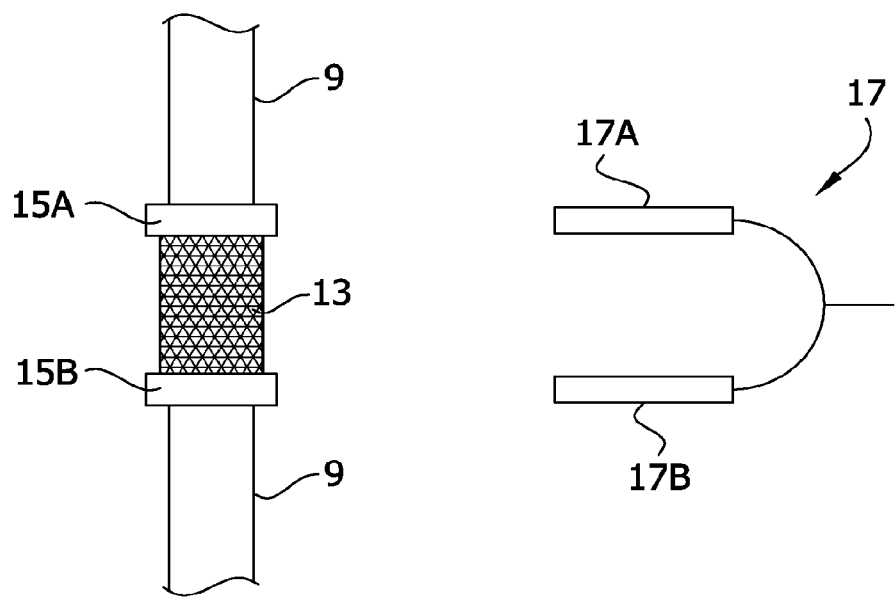
FIG. 5 is a diagram of an embodiment of a mounting member and identification members of the feeding set and further illustrating a related reader device.

As shown in FIGS. 2 and 5, the mounting member 13 is configured to engage mount 45 of the pump 1 when loading the feeding set 5 on the pump such that the reader 17 may detect the presence of the identification member 15 attached to the mounting member 13. The reader 17 may be disposed on, in, or near the mount 45 to detect the presence of the identification member 15. In the illustrated embodiment, identification member 15 comprises a first identification component 15A and a second identification component 15B. Any number of identification components is envisioned. The reader 17 may comprise a pair of reader devices 17A, 17B that detect the identification components 15A, 15B, respectively. It will be understood that the number of reader devices 17 may be the same as the number of identification components 15. The identification components 15A, 15B may be magnetic components or, in the alternative, magnetically susceptible metallic components capable of detection by reader devices 17A, 17B, respectively without requiring direct physical contact with the reader. The reader devices 17A, 17B may preferably be Hall-effect sensors or other types of proximity sensors that are positioned near the mount 45 such that the reader devices 17A, 17B can detect the presence of the identification components 15A, 15B when the mounting member 13 is engaged to the mount or at least the magnetic field of any of the one or more identification components. Other types of readers may be used. For example, the readers may rely on optically identifying any of the one or more identification components. The identification member 15 can be mounted directly on the cassette 9 and the reader 17 can be positioned to detect the presence of the identification member on the cassette when the cassette is received in the recess 7 of the pump 1.

Upon engagement of the mounting member 13 to the mount 45, reader devices 17A, 17B may be capable of identifying identification data represented by the number and position of the identification components 15A, 15B. In particular, the attachment of one or more identification components 15A, 15B to the mounting member 13 provides a means for allowing software subsystem 47 (FIG. 4) to identify information related to a nutritional liquid associated with the feeding set 5 loaded on the pump 1. Referring to FIG. 5, the mounting member 11 may have one or more identification components 15A, 15B (two are shown in FIG. 5) attached thereto in accordance with an identification scheme that permits software subsystem 47 to identify at least one characteristic of the nutritional liquid associated with the feeding set 5 loaded on the pump 1. In order to identify the at least one characteristic of the nutritional liquid, a processor such as microprocessor 49 may be operatively associated with memory 51 containing one or more identification schemes for identifying different characteristics of the nutritional liquid. The memory 51 may also contain a library of nutritional liquids associated with various types of cassettes and feeding sets for use with the pump 1. The identification scheme may involve utilizing the relative positional interaction of any or all the readers as identifiably associated with a corresponding identification component. Thus, for example, in a reader assembly having an arrangement of two reader components, if a first reader component proximally detects the presence of an appropriate first identification component and a second reader component proximally detects the presence of an appropriate second identification component, the identification member provides a first representation of a first nutritional liquid, or family of nutritional liquids. Further, if the first reader component proximally detects the presence of an appropriate first identification component and the second reader component fails to detect the proximal presence of an appropriate second identification component, the identification member provides a representation of a different nutritional liquid, or family of nutritional liquids. Accordingly, the processor can thus associate the corresponding nutritional liquid through the respective representation from corresponding identification member to at least one characteristic of the liquid. The reader may be implemented with three or more components.

The at least one characteristic may include at least any one or more of a brand or brand name of the nutritional liquid to be delivered through the feeding set 5, and may include at least one or more data associated parameters such as but not limited to nutritional liquid type, caloric intake requirement, fat intake requirement, protein intake requirement, mineral intake requirement, vitamin intake requirement, and a patient group associated with the nutritional liquid. The at least one characteristic may also include at least one data parameter pertaining to at least one of a viscosity, an osmolality, a digestibility, a caloric content, a protein content, a sugar content, a fat content, fiber content, a free water content, a carbohydrate content, a cholesterol content, an amino acid content, a vitamin content, a mineral content, a nitrogen content, a sodium content, a potassium content, a chloride content, a calcium content, a magnesium content, an electrolyte content, and a nutritional requirement of the nutritional liquid.

The at least one characteristic may also include a family of nutritional liquids associated with the feeding set 5. The family of nutritional liquids may be a subset of nutritional liquids within the library of nutritional liquids stored in the memory 51, such as nutritional liquids available from a particular provider. By representing a characteristic of the nutritional liquid associated with the feeding set 5 with the number and position of the identification components 15A, 15B, the user is not required to scroll through a large database of formulas. Instead, the subset of the full library of formulas is displayed on the display screen 21 from which the user may select the nutritional liquid that will be delivered.

FIG. 6 illustrates a sequence of steps software subsystem 47 may execute through microprocessor 49 to recognize and incorporate the at least one characteristic of the nutritional liquid associated with the feeding set 5 loaded to the pump 1. At decision point 318, software subsystem 47 may determine whether a feeding set 5 is loaded to the pump 1 by detecting engagement of the mounting member 13 to the pump. In particular, the microprocessor 49 may monitor a signal from the reader devices 17A, 17B indicating identification components 15A, 15B are engaged to the pump 1. If the feeding set 5 is not loaded, then the pump 1 remains inoperative, at step 320. However, if the feeding set 5 is loaded to the pump 1, at 324 the microprocessor 49 may determine the at least one characteristic of the nutritional liquid associated with the feeding set 5 by detecting the location and number of identification components 15 detected by the reader 17. Each different characteristic may have a predetermined number and location of identification components attached to the mounting member 13.

For example, at decision point 324, if reader 17 detects both identification component 15A and 15B, the software subsystem 47 may identify a first characteristic of the nutritional liquid associated with the feeding set 5. If the reader 17 detects only identification component 15B, the software subsystem 47 may identify a second characteristic of the nutritional liquid different from the first characteristic. If the reader 17 detects only identification component 15A, the software subsystem 47 may identify a third characteristic of the nutritional liquid different from the first and second characteristics. Any number of identification components and reader devices may be used to identify any number of characteristics of a nutritional liquid associated with the feeding set 5. Other types of identification members can be used, including without limitation, members of differing shapes and emitting different electromagnetic signals.

Once software subsystem 47 identifies the at least one characteristic of the nutritional liquid associated with the feeding set 5 loaded to the pump 1, the microprocessor 49 may adjust the flow rate of the pump 1 to achieve a target feeding rate specific to the feeding set 5 loaded to the pump and the nutritional liquid associated with the feeding set. Thus, software subsystem 47 is able to not only detect that the feeding set 5 is loaded, but also determine and implement nutritional liquid data to automatically control fluid flow through the feeding set upon loading the feeding set to the pump 1.

Referring to FIGS. 4 and 6, the memory 51 can store a set of instructions 53 for determining a flow rate for the pump 1 based on the at least one characteristic of the nutritional liquid represented by identification components 15 and retrieved by the microprocessor 49. In order to control the flow rate of the pump 1, at 326, the microprocessor 49 retrieves from the memory 51 the set of instructions 53 for implementing the information data represented by the identification components 15. At 328, the microprocessor 49 may apply the data to the set of instruction in the memory 51 to determine a flow rate of the pump 1. At 330, the microprocessor 49 may adjust the motor output to produce the flow rate determined at 328 to achieve a target-feeding rate. For example, by knowing the viscosity of the nutritional liquid the amount of rotation may be altered to assure the correct quantity of nutritional liquid is delivered.

Upon determining the operating flow rate, at 332, the microprocessor 49 can send instructions to monitor the pumping parameters and intermittently, continuously, or continually adjust the instantaneous operating flow rate for the pump 1 to achieve the target-feeding rate. The microprocessor 49 may keep track of the volume of feeding fluid delivered to the patient, and the number of calories delivered to the patient. Other feeding parameters, such as but not limited to elapsed time, remaining time, and fat content delivered, may also be monitored and optionally displayed through, for example, the user interface 19. Compliance monitoring can be performed by comparing the monitored pumping parameters (e.g., volume of fluid delivered, number of calories delivered, etc.) to target pumping parameters to assess whether the target pumping parameters are being met and/or a prescribed treatment regimen is being followed. Results of the compliance monitoring can be stored in the memory 51 for review by the clinician. The data can also be stored in the memory 51 for wireless data mining, service modules, and/or asset tracking purposes.

It is to be understood that in the described embodiment, the software subsystem 47, the microprocessor and memory 51 may be broadly considered "a control circuit." These components may be individually considered "a control circuit." Moreover, other types of control circuits may be used within the scope of the present invention.

The memory 51 can comprise one or more non-volatile memory components, e.g., ROM, PROM, EPROM, EEPROM, and flash memory. In other configurations, other types of non-volatile memory components can be utilized in addition to or instead of the non-volatile memory components such as but not limited to removable or portable data storage devices, such as hard disk drives, optical disk, magnetic tape, holographic memory, and memory cards. Alternatively or in addition, memory 51 can comprise one or more volatile memory components such as but not limited to random access memory (RAM), dynamic random access memory (DRAM), and static random access memory (SRAM).

Embodiments of the invention may be described in the general context of computer-executable instructions, such as program modules, executed by one or more computers or other devices. The computer-executable instructions may be organized into one or more computer-executable components or modules including, but not limited to, routines, programs, objects, components, and data structures that perform particular tasks or implement particular abstract data types. Aspects of the invention may be implemented with any number and organization of such components or modules. For example, aspects of the invention are not limited to the specific computer-executable instructions or the specific components or modules illustrated in the figures and described herein. Other embodiments of the invention may include different computer-executable instructions or components having more or less functionality than illustrated and described.

Further, the order of execution or performance of the operations in embodiments of the invention illustrated and described herein is not essential, unless otherwise specified. That is, the operations may be performed in any order, unless otherwise specified, and embodiments of the invention may include additional or fewer operations than those disclosed herein. For example, it is contemplated that executing or performing a particular operation before, contemporaneously with, or after another operation is within the scope of aspects of the invention.

In operation, the microprocessor 49 executes computer-executable instructions such as those illustrated in the figures to implement aspects of the invention. Aspects of the invention may also be practiced in distributed computing environments where tasks are performed by remote processing devices linked through a communications network. In a distributed computing environment, program modules may be located in both local and remote computer storage media including memory storage devices.

Further aspects of the invention can pertain to methods related to facilitating use of enteral feeding pumps. For example, the method can comprise, in accordance with one or more embodiments, providing a conduit assembly including tubing fluidly connectable to a container wherein the tubing can be adapted for mounting on the enteral feeding pump to provide a fluid pathway for delivering nutritional liquid from the container to a patient when the tubing; and providing an identification member associated with the conduit assembly, which can be mountable on the conduit assembly, having information regarding at least one characteristic of a nutritional liquid associable with the feeding set. In some cases, the method can involve positioning the identification member on the conduit assembly so as to permit acquisition of the information and identification by the enteral feeding pump of the at least one characteristic of the nutritional liquid upon mounting the conduit assembly on the enteral feeding pump.

Still further aspects can pertain to revising the library or at least a portion of the stored information of the library of formula. For example, the enteral feed pump can have at least one user interface that can be utilized to enter or update the library information. In some cases, the enteral feeding pump can have a data port that can facilitate data transfer from an external device to the memory device in the pump that stores the library information. For example, the enteral feeding pump can have a USB port configured through the controller to transfer data from an external device to replace at least a portion of the memory of the pump. An alternative configuration can involve utilizing wired Ethernet local area networks based on, for example, the IEEE 802.3 standard to effect the transfer. In still other cases, the enteral feeding pump can be in wireless communication with a remote device having updated library information. In such an exemplary architecture, data transfer from the remote device can be effected through wireless communication in accordance with any commercially utilized protocols such as but not limited to any one or more of cellular data transmission and wireless radio such as Wi-Fi based on any of the IEEE 802.11 standards. Preferable configurations can further involve transmitting, wired or wirelessly at least a portion of the library in encrypted form. Such aspects can be particularly advantageous when utilized to tailor the feeding rate based on the fluid to be delivered and patient or user needs. For example, a particular predetermined delivery protocol may be implemented for a patient and updated upon the discretion of a caregiver from a remote facility or location. Thus, such a feature can advantageously further assure or at least increase the likelihood of utilizing a predetermined delivery protocol with a nutritional liquid.

Further embodiments may implemented to utilize a remote facility to provide the predetermined protocol. For example, in a feeding pump connected to the remote facility, the pump may identify the representation of the nutritional liquid and transmit such information to the remote facility. In response, the remote facility may then receive the representation information and establish a predetermined delivery protocol from a database, and transmit a predetermined delivery protocol to achieve one or more treatment targets based, at least partially, on the received representation information.

Other operations may be implemented including, for example, identifying the frequency of nutritional liquid delivery, the amount of nutritional liquid delivered, and the type of nutritional liquid delivered, which, in turn, can facilitate any one or more of asset tracking, e.g., determining whether a patient has used or consumed a sufficient amount of nutritional liquid, or type of nutritional liquid, whether the patient has any of such nutritional liquid remaining, or type of nutritional liquid remaining, and whether the patient requires additional nutritional liquid at the patient's location.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above constructions and methods without departing from the scope of the invention, it is intended that all matter contained in the above description and shown in the accompanying drawings shall be interpreted as illustrative and not in a limiting sense.

What is claimed is:

1. A feeding set for use with a feeding pump to deliver nutritional liquid to a patient, the feeding set comprising:
   a container to store the nutritional liquid;
   tubing in fluid communication with the container and being adapted for mounting on the feeding pump, the tubing providing a fluid pathway for delivering the nutritional liquid from the container to the patient; and
   an identification member representative of the nutritional liquid in the container, the identification member configured to permit identification by the feeding pump of at least one characteristic of the nutritional liquid upon mounting of the identification member on the feeding pump, the at least one characteristic of the nutritional liquid comprising at least one of a nutritional content, a fluid flow property, and a brand or brand name of the nutritional liquid.

2. The feeding set of claim 1, further comprising a cassette connected to the tubing.

3. The feeding set of claim 2, wherein the identification member is mounted on the cassette.

4. The feeding set of claim 1, wherein the identification member comprises at least one magnet arranged to represent the nutritional liquid in the container.

5. The feeding set of claim 4, wherein the identification of the at least one characteristic is based on a number and relative positions of the at least one magnet.

6. The feeding set of claim 1, wherein the fluid flow property comprises a viscosity of the nutritional liquid.

7. The feeding set of claim 1, wherein the nutritional content comprises a caloric content of the nutritional liquid.

8. The feeding set of claim 1, wherein a family of the nutritional liquids associated with the feeding set is represented by the identification member.

9. A method of detecting a characteristic of a nutritional liquid associated with a feeding set connected to a feeding pump, the method comprising:
 mounting a feeding set on a housing of the pump, the pump configured to act on the feeding set to produce flow of a nutritional liquid from a container through the feeding set during operation of the pump;
 detecting engagement of the feeding set with the housing of the pump, the feeding set including at least one identification component representative of the nutritional liquid in the container;
 reading the at least one identification component to identify at least one characteristic of the nutritional liquid associated with the feeding set, the at least one characteristic of the nutritional liquid comprising at least one of a nutritional content, a fluid flow property, and a brand or brand name of the nutritional liquid; and
 identifying, with a processor connected to a reader of the pump, the at least one characteristic of the nutritional liquid upon detecting the engagement of the feeding set with the housing of the pump.

10. The method of claim 9, wherein the processor identifies the at least one characteristic based on a number and relative positions of the at least one identification component.

11. The method of claim 9, wherein the at least one identification component comprises at least one magnet arranged to represent the nutritional liquid in the container.

12. The method of claim 9, wherein the nutritional content comprises a free water content of the nutritional liquid.

13. The method of claim 9, wherein the processor controls flow of the nutritional liquid through the feeding set based on the identified at least one characteristic.

14. The method of claim 9, wherein the pump is linked to a communications network.

15. The method of claim 9, further comprising wirelessly communicating at least one of a frequency of delivery of the nutritional liquid, an amount of the nutritional liquid delivered, and a type of the nutritional liquid delivered.

16. The method of claim 9, wherein the pump automatically determines a flow rate for delivering the nutritional liquid through the feeding set based on the at least one characteristic of the nutritional liquid identified by the reader upon the engagement of the feeding set with the housing.

17. The method of claim 9, wherein the pump automatically initiates a compliance operation including monitoring of a volume of the nutritional liquid and a number of calories delivered to a patient through the feeding set upon engagement of the feeding set with the housing.

18. A feeding set for use with a feeding pump to deliver nutritional liquid to a patient, the feeding set comprising:
 a container configured to store the nutritional liquid;
 tubing in fluid communication with the container and being adapted for mounting on the feeding pump, the tubing providing a fluid pathway for delivering the nutritional liquid from the container to the patient;
 a cassette connected to the tubing; and
 an identification member mounted on the cassette, the identification member representative of at least one of a nutritional content, a fluid flow property, and a brand or brand name of the nutritional liquid in the container.

19. The feeding set of claim 18, wherein the identification member includes at least one magnet, and the identification of the type of the nutritional liquid is based on a number and relative positions of the at least one magnet.

* * * * *